(12) United States Patent
Suri et al.

(10) Patent No.: US 7,832,114 B2
(45) Date of Patent: Nov. 16, 2010

(54) TRACKER HOLDER ASSEMBLY

(75) Inventors: Jasjit S. Suri, Roseville, CA (US);
Dinesh Kumar, Grass Valley, CA (US);
Animesh Khemka, Grass Valley, CA (US)

(73) Assignee: Eigen, LLC, Grass Valley, CA (US)

( * ) Notice: Subject to any disclaimer, the term of this patent is extended or adjusted under 35 U.S.C. 154(b) by 286 days.

(21) Appl. No.: 11/850,482

(22) Filed: Sep. 5, 2007

(65) Prior Publication Data
US 2008/0249403 A1    Oct. 9, 2008

Related U.S. Application Data

(60) Provisional application No. 60/949,257, filed on Jul. 12, 2007, provisional application No. 60/910,170, filed on Apr. 4, 2007.

(51) Int. Cl.
*A61B 8/00*    (2006.01)
(52) U.S. Cl. .......................... 33/503; 600/437
(58) Field of Classification Search ............... 33/503; 600/437, 459; 606/130
See application file for complete search history.

(56) References Cited

U.S. PATENT DOCUMENTS

| | | | |
|---|---|---|---|
| 5,170,790 A | | 12/1992 | Lacoste et al. |
| 5,230,623 A | * | 7/1993 | Guthrie et al. ................ 433/72 |
| 5,282,472 A | | 2/1994 | Companion et al. |
| 5,398,690 A | | 3/1995 | Batten et al. |
| 5,494,039 A | | 2/1996 | Onik et al. |
| 5,824,007 A | * | 10/1998 | Faraz et al. ................ 606/130 |
| 6,046,727 A | * | 4/2000 | Rosenberg et al. .......... 345/156 |
| 6,171,249 B1 | | 1/2001 | Chin et al. |
| 6,179,262 B1 | | 1/2001 | Ellard et al. |
| 6,246,200 B1 | * | 6/2001 | Blumenkranz et al. . 318/568.11 |
| 6,261,234 B1 | | 7/2001 | Lin |
| 6,301,989 B1 | | 10/2001 | Brown et al. |
| 6,325,760 B1 | | 12/2001 | Takanori et al. |
| 6,360,027 B1 | | 3/2002 | Hossack et al. |
| 6,378,376 B1 | | 4/2002 | Derman et al. |
| 6,423,009 B1 | | 7/2002 | Downey et al. |
| 6,425,865 B1 | | 7/2002 | Salcudean et al. |
| 6,447,447 B1 | | 9/2002 | Mitsumori |
| 6,451,027 B1 | | 9/2002 | Cooper et al. |
| 6,620,111 B2 | | 9/2003 | Stephens et al. |
| 6,931,745 B2 | * | 8/2005 | Granger ...................... 33/503 |
| 7,008,373 B2 | | 3/2006 | Stoianovici et al. |

(Continued)

FOREIGN PATENT DOCUMENTS

WO    2007045810 A2    4/2007

(Continued)

*Primary Examiner*—G. Bradley Bennett
*Assistant Examiner*—Tania C Courson
(74) *Attorney, Agent, or Firm*—Marsh Fischmann & Breyfogle LLP

(57) ABSTRACT

Provided herein are devices and methods for mounting variously configured medical imaging probes to a tracker assembly for imaging applications. In one aspect, a tracker assembly provides multiple degrees of freedom for positioning a probe relative to a patient and/or maintaining a probe in a desired location for imaging purposes. The tracker generates location information that may be utilized as frame of reference information for acquired images. In another aspect a holding device allows for interfacing/holding differently configured probes in a common orientation to a predetermined frame of reference.

12 Claims, 17 Drawing Sheets

U.S. PATENT DOCUMENTS

| | | |
|---|---|---|
| 7,108,660 B2 | 9/2006 | Stephens et al. |
| 7,189,246 B2 | 3/2007 | Otsuka et al. |
| 7,255,310 B2 | 8/2007 | Niwa et al. |
| 7,287,310 B2 | 10/2007 | Zuzelo |
| 7,412,776 B2 * | 8/2008 | Iikubo et al. .................. 33/503 |
| 2005/0075536 A1 * | 4/2005 | Otsuka et al. ............... 600/102 |
| 2005/0159676 A1 | 7/2005 | Taylor et al. |
| 2008/0004481 A1 | 1/2008 | Bax et al. |
| 2008/0269604 A1 * | 10/2008 | Boctor et al. ............... 600/437 |
| 2010/0036245 A1 * | 2/2010 | Yu et al. ..................... 600/439 |

FOREIGN PATENT DOCUMENTS

| | | |
|---|---|---|
| WO | 2007147232 A1 | 12/2007 |

\* cited by examiner

2D Image Storage

3D Volume Image

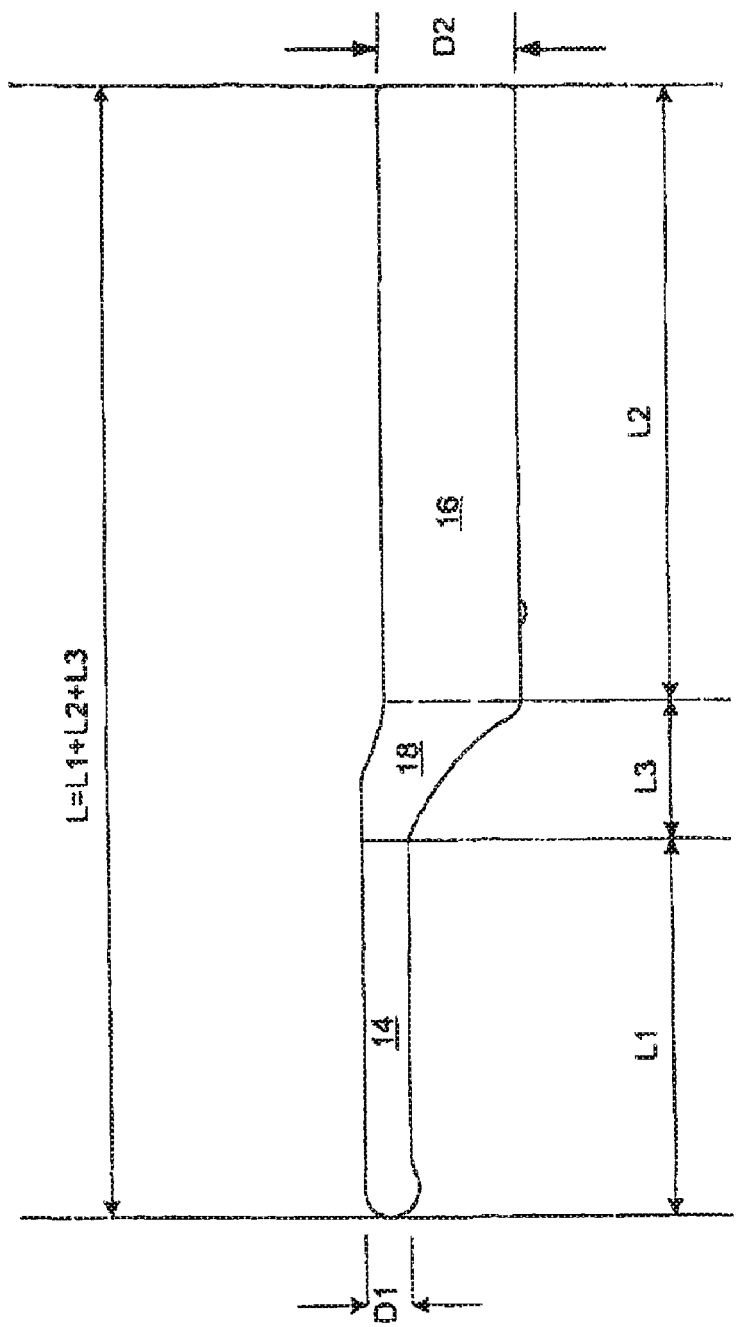

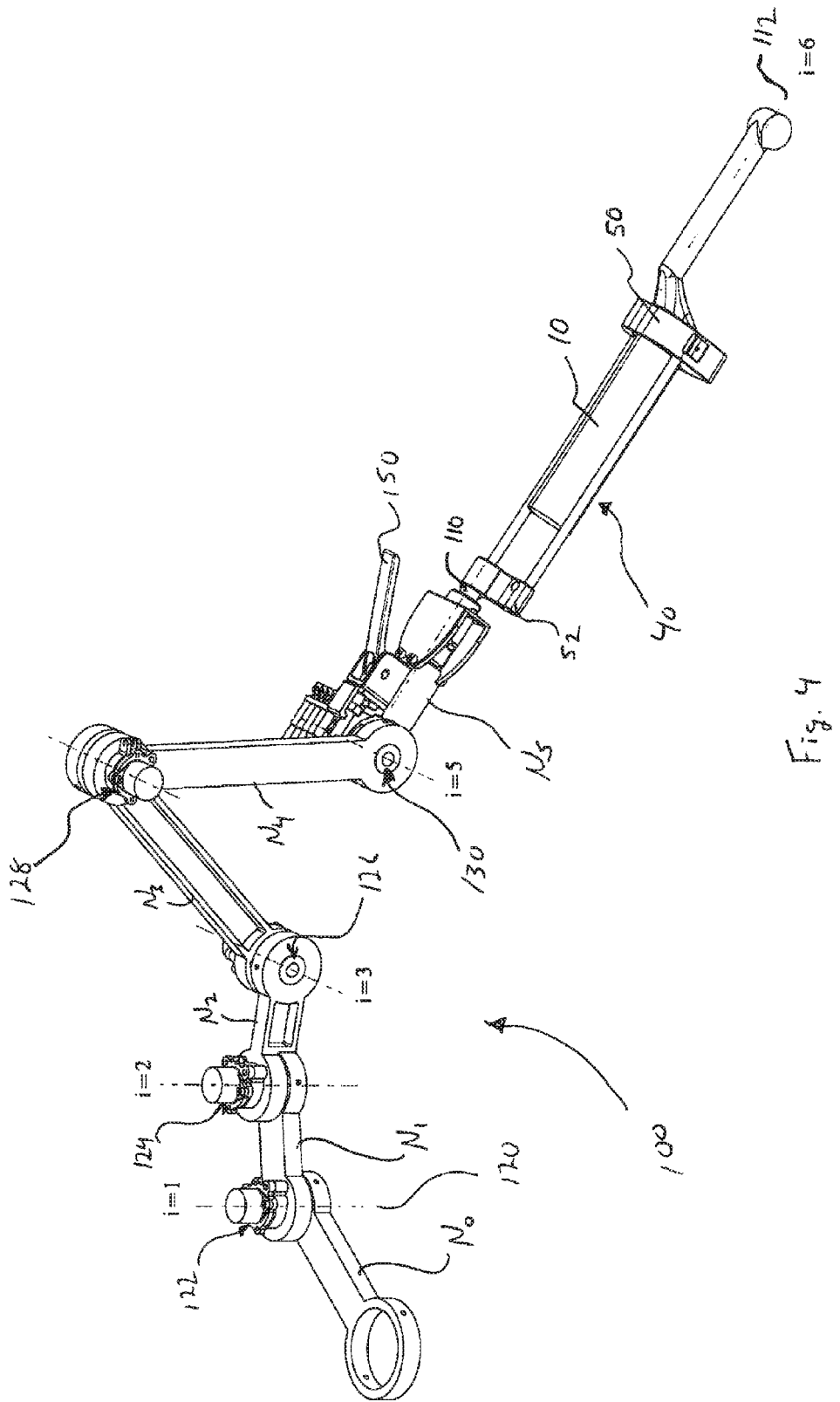

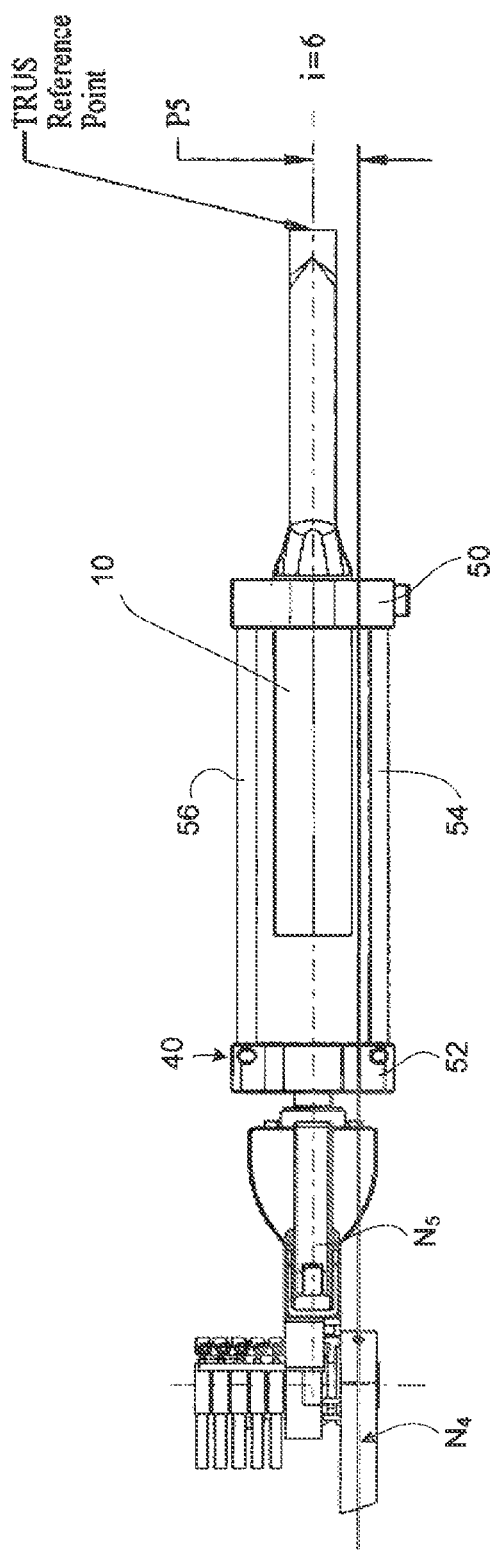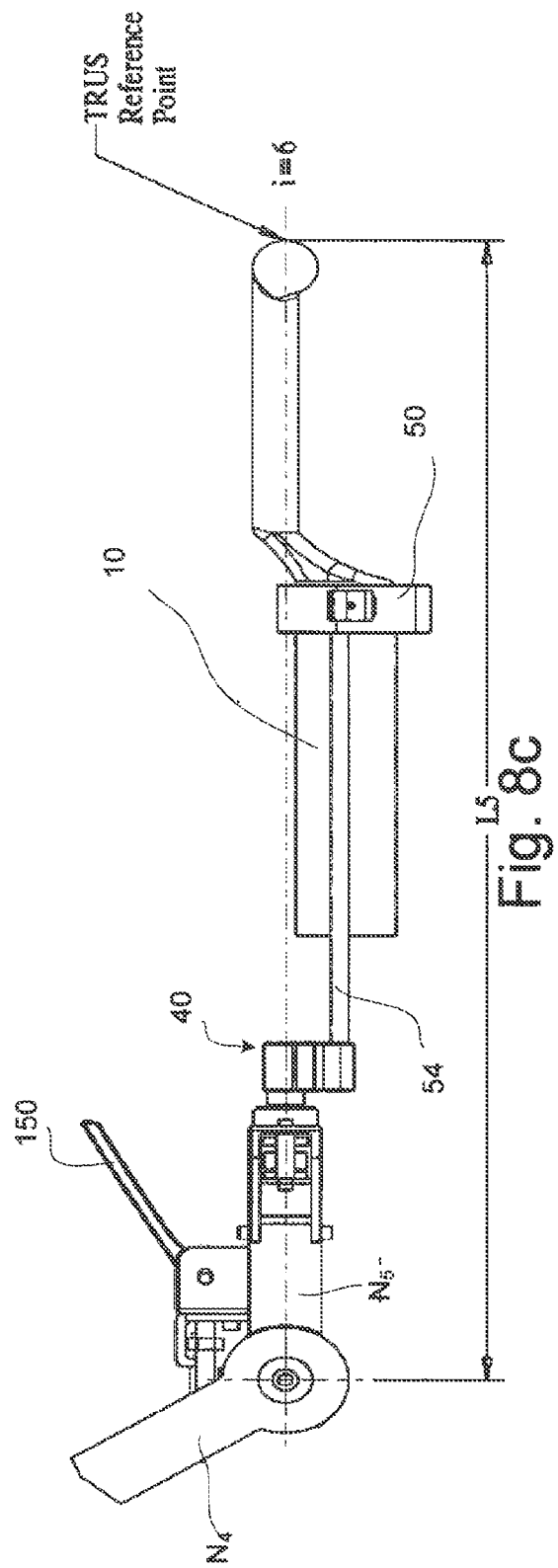
Fig. 8c

TRACKER HOLDER ASSEMBLY

CROSS REFERENCE TO RELATED APPLICATIONS

This application claims the benefit of the filing date of U.S. Provisional Patent Application No. 60/949,257 entitled "Ultrasound Holders and Rotation Device" and having a filing date of Jul. 12, 2007 and also claims the benefit of the filing date of U.S. Provisional Patent Application No. 60/910,170 entitled "Tracker Holder Assembly" and having a filing date of Apr. 4, 2007 the entire contents of both of which are incorporated herein by reference.

FIELD OF INVENTION

The present invention is directed to system, apparatus and method for holding and positioning a medical imaging instrument. More particularly, the invention relates to an apparatus adapted to hold a plurality of differently configured medical imaging instruments such that those instruments may be positioned, secured and/or rotated about at least one fixed axis by a positioning/tracking system.

BACKGROUND OF THE INVENTION

Medical imaging instruments are often utilized by doctors and other medical professionals to conduct non-invasive examinations. That is, medical imaging instruments, including X-ray, magnetic resonance (MR), computed tomography (CT), ultrasound, and various combinations of these instruments/techniques are utilized to provide images of internal patient structure for diagnostic purposes as well as for interventional procedures. Such medical imaging instruments allow examination of internal tissue that is not readily examined during normal visual or tactile examination. Applications include imaging in the areas of urology and brachytherapy.

Medical imaging devices typically allow for generating 3-D images of internal structures of interest. Such 3-D imaging may improve the accuracy and/or reliability of medical diagnosis. For instance, a medical imaging device may be utilized to generate a 3-D model or map of the prostate such that one or more biopsies may be taken from a desired location of the prostate. For purposes of prostate imaging, image acquisition and guidance may be provided by a transrectal ultrasound-imaging device (TRUS). In such an application, the ultrasound-imaging device may be inserted into the rectum of a patient to generate an image. Such images may be utilized to take one or more biopsies from a prostate location of interest and/or implant radioactive seeds at one or more desired locations in a brachytherapy procedure.

In order to generate 3-D images, many medical imaging devices obtain a plurality of images (e.g., two dimensional images) and combine these images together to form a 3-D image. Accordingly, movement of a medical imaging device between the acquisition of individual images makes it more difficult to properly align (e.g., register) the different images for purposes of generating accurate 3-D images.

Traditionally, a medical practitioner has manipulated a medical imaging instrument by hand for medical image acquisition and/or treatment. That is, the medical practitioner manually guides the instrument. Such manual manipulation is suitable for many medical procedures. However, in instances where it is desirable to obtain multiple images for 3-D image generation, manual manipulation of the device may result in movement between images. Further, for biopsy and other treatment procedures it is desirable that the relative location between an imaging instrument and a tissue area of interest be known. That is, it is important that the device directs an imaging field to a particular tissue location and remain stationary to allow for guiding a biopsy/treatment device to a tissue location within the imaging field. Relative movement between the imaging device and the tissue area of interest during imaging and/or biopsy/treatment may impede the successful performance of these procedures.

Accordingly, a number of holding and manipulating/positioning assemblies have been proposed wherein a holder interfaces with an imaging device such as an ultrasound probe. Such a holder is then interconnected to one or more mechanical armatures and/or actuators such that the probe may be mechanically positioned and/or rotated. However, original equipment manufactures (OEMs) of ultrasound probes do not have a standardized design. As will be appreciated, ultrasound probes generated by different manufactures come in different lengths and widths. This is true for both the insertion portion end of a probe as well as a handle portion of the probe. This has resulted in the need for specialized positioning assemblies for differently configured ultrasound probes. Accordingly, prior positioning assemblies have required that a medical facility utilize a particular probe with a particular positioning assembly.

SUMMARY OF THE INVENTION

Provided herein are devices and methods for positioning variously configured medical imaging devices for imaging applications. In one aspect, a holding device allows for interfacing/holding differently configured ultrasound probes such that the probes may be attached to a positioning device using a common interface. In another aspect, the positioning device may allow for positioning and/or fixedly supporting an imaging device relative to a patient. The positioning device may also provide location information for the imaging device. In this regard, a computer may be provided for executing software for utilizing outputs of the positioning device to calculate a position of a supported medical imaging device and/or utilize such outputs with acquired images. It will be appreciated that the positioning and holding devices may be utilized alone and/or in conjunction. In this regard, it is believed that each device contains novel aspects alone as well as in combination.

According to a first aspect, a device for positioning and tracking the position of a medical imaging device in three dimensions is provided. The device includes a base element that is adapted for fixed connection relative to a frame of reference. For instance, such a base element may be affixed to an examination table within an imaging area. A linkage having at least three rigid arms that are hingedly connected and extend from the base element. In this regard, a first end of a first linkage may be hingedly interconnected to the base element, and a second end of the linkage may be free to move in three dimensions. Encoders are disposed between each of the hinged connections of the linkages and/or the base element that generate outputs indicative of the angular position between each pair of hingedly connected elements. As the lengths of the rigid arms of the linkage are known, the outputs of the encoders may be utilized in conjunction with such lengths to calculate the location of the free end of the linkage relative to the base element. Accordingly, such information may be utilized to determine the position of, for example, an ultrasound probe supported by the linkage anchor for use in registering images generated by that probe to a frame of reference.

In one arrangement, the free end of the linkage further includes a rotational shaft and an encoder operative to generate an output indicative of the rotation of that rotational shaft. In this regard, it will be appreciated that a holder for holding an ultrasound probe may be interconnected to the rotational shaft. In this regard, the linkage may be utilized to position a probe to an imaging location. The probe may then be rotated about the rotational axis to generate, for example, a plurality of two-dimensional images that may be utilized to generate a three-dimensional image.

In one arrangement, each of the hinged connections between the linkages and the base element comprise a joint that limits movement between interconnected elements to rotation about a single axis (i.e, a single degree of freedom). In this regard, it will be appreciated that movement about a single axis allows for reducing the complexity of calculations required to calculate the location of the free end of the linkage. In one arrangement, at least first and second joints define a first set of parallel axes and third and forth joints define a second set of parallel axes. These sets of parallel axes may be transverse. In this regard, the first set of joints may allow for positioning the linkage end, for example, in an XY coordinate system. Likewise, the second set of joints may allow for positioning the linkage in, for example, a YZ coordinate system. In any case, the use of such transversely aligned joints allows for three-dimensional movement of the distal end of the linkage.

In one arrangement, the linkage includes at least five linkage members and five hinged connections. In such an arrangement, the last linkage (i.e., the free end) may be operative to rotate around the axis. In such an arrangement, the linkage may allow the free end of the linkage to move with six degrees (6°) of freedom. It will be appreciated that each hinged connection between linkage members adds another degree of freedom and extension, Accordingly, using multiple linkage members (e.g., 3 or more) the range of motion for the linkage is quite large. In another arrangement, the linkage members of the device may be counterbalanced via spring loading mechanism associated with the hinged connections and/or using counterweights. As a result, the operator does not have to support any weight and hence, the device is easy to use. The unconstrained motion of the device makes it well suited for a variety of applications.

In a further arrangement, each hinged connection includes a breaking mechanism that allows for limiting movement of the hinged connection. In this regard, the linkage may be moved to a desired location, and the breaking mechanisms may be actuated in order to maintain the linkage at a desired location in three-dimensions. At such time, a supported imaging device may be rotated around the rotational axis of the free end of the last linkage. In one arrangement, all the breaking mechanisms may be interconnected to a single actuator such that a user may lock the linkage in a desired position utilizing, for example, a single break lever. Single action locking mechanism that locks all the degree of freedoms at once is ideally suited for procedures where the operator can align the imaging device in a certain position and lock it in place. After locking, the operator is free to use both hands for performing a procedure.

The encoders may be any device that generates an output that is indicative of the angular movement between hingedly connected elements. In one arrangement, magnetic encoders are utilized wherein a magnet and a reader are utilized to determine angular motion between hingedly and/or pivotally connected elements. To provide a high degree of resolution, in one arrangement, the magnetic encoders have at least 12-bit resolution.

In one arrangement, the device is a mechanical device and hence is less noise sensitive compared to, for example, optical trackers. Likewise, it does not cause interference compared to magnetic and/or electrically actuated trackers. The setup and manufacturing is easier than the magnetic tracker while the cost is also much lower.

According to another aspect, an apparatus for interfacing with an ultrasound probe is provided. The apparatus includes a collar for receiving a portion of an ultrasound probe. The collar includes a first body member and a second body member. These body members are releaseably interconnectable and define an aperture for receiving at least a portion of an ultrasound probe when interconnected. The apparatus further includes an interface element for interfacing with a positioning device and at least one connecting member that extend between the interface element and the collar. This connecting member may be releaseably connected to the collar and/or the interface element. In this regard, the interface element and connecting member may be a standardized interface for use with a positioning/tracker device. Likewise, the collar may be individualized for individual probes (e.g. probes of different OEM manufacturers). Accordingly, a collar may be selected for a particular probe, engaged with the probe and then interfaced with the remainder of the apparatus.

In order to securely support the probe, the inside surfaces of the first and second body members that define the aperture may be conformably shaped to receive a particular ultrasound probe. Further, the aperture of the collar defined by the first and second body members may be designed such that the imaging portion of a probe (e.g., an insertion axis of a probe) may be aligned with the rotational axis defined by the interface element, which interfaces with the positioning device. In this regard, when a probe is supported by the apparatus and interconnected to a positioning device, the probe may be held in alignment with the rotational axis of the positioning device.

BRIEF DESCRIPTION OF THE DRAWINGS

FIG. 2b illustrates a 3-D volume image generated from the two dimensional images of FIG. 2a.

FIG. 3 illustrates an exemplary ultrasound probe.

FIG. 4 illustrates a tracker holder assembly.

FIGS. 8A-8C illustrate dimensions of the tracker assembly utilized to calculate the position of the free end of the tracker assembly.

DETAILED DESCRIPTION

Reference will now be made to the accompanying drawings, which assist in illustrating the various pertinent features of the present disclosure. Although the present disclosure is described primarily in conjunction with transrectal ultrasound imaging for prostate imaging, it should be expressly understood that aspects of the present invention may be applicable to other medical imaging applications. In this regard, the following description is presented for purposes of illustration and description.

Disclosed herein are systems and methods that facilitate obtaining medical images and/or performing medical procedures. In one embodiment, a medical imaging device holder (i.e., holding device or cradle) is provided that is adapted to securely support multiple differently configured ultrasound probes. In another embodiment, a multi-linkage tracker assembly is provided for positioning an imaging device relative to a patient and maintaining the imaging device in a fixed position.

The probe holder may be interfaced with the tracker assembly such that a supported probe may be rotated about a fixed axis. In this regard, multiple images may be obtained from the supported probe in different angular positions for 3-1) image generation. As the probe is securely supported by the tracker device, there may be little or no probe movement, other than about the fixed axis of rotation, between successive images. Accordingly, successive images may more easily be registered together. In other instances, the tracker assembly may be utilized to securely position a probe relative to a tissue area of interest while a medical instrument is guided to the area of interest.

Figure 1A:
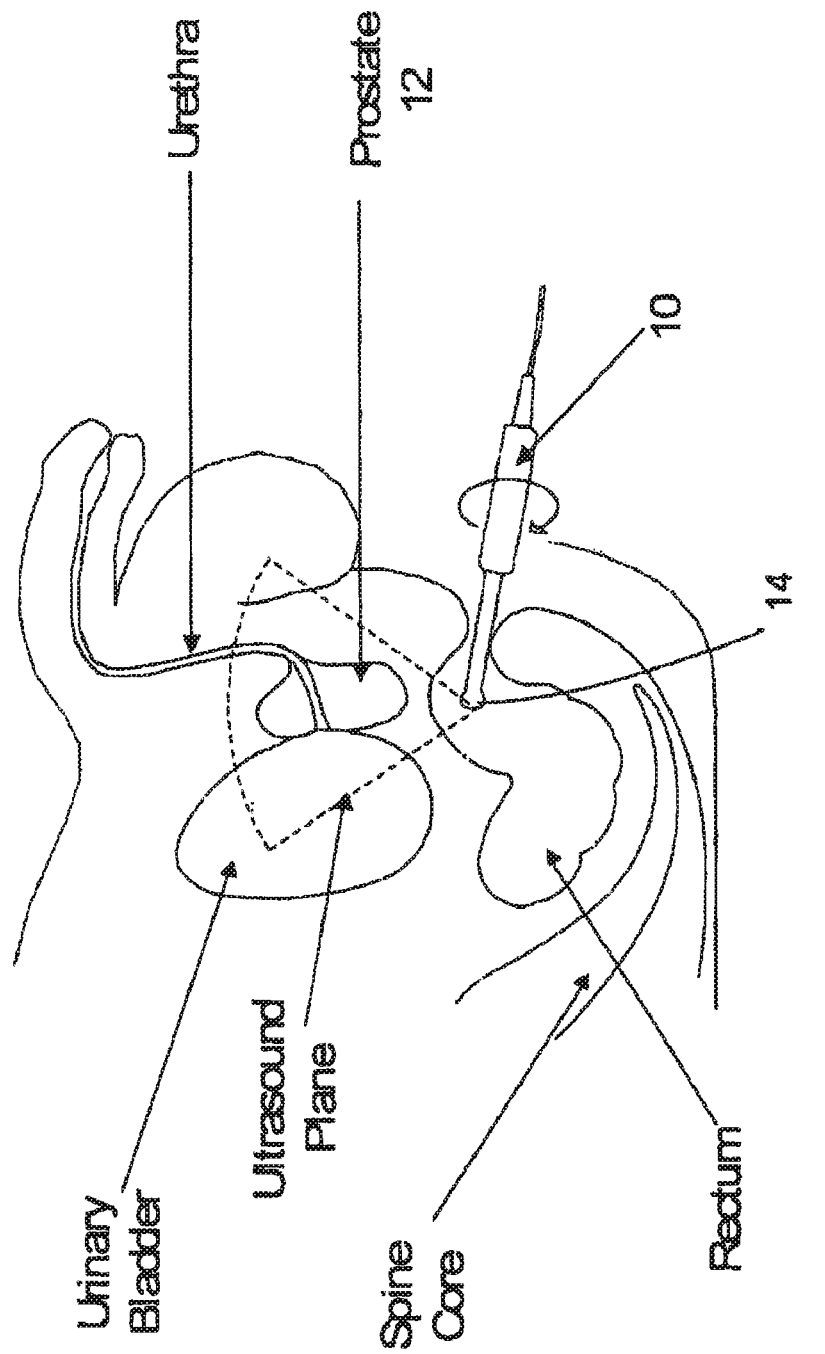
FIG. 1A shows a cross-sectional view of a trans-rectal ultrasound imaging system as applied to perform prostate imaging.
Figure 2A:
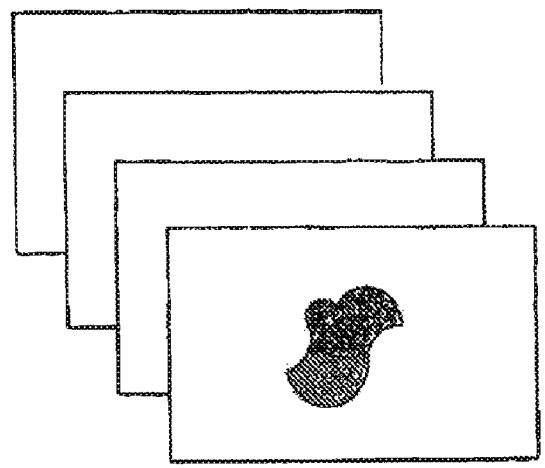
FIG. 2a illustrates two-dimensional images generated by the TRUS of FIG. 1.
Figure 2B:
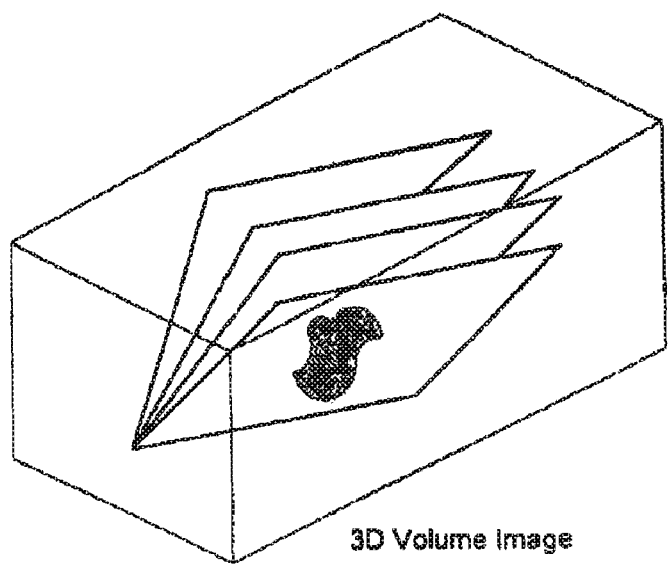

FIG. 1A illustrates a transrectal ultrasound probe being utilized to obtain a plurality of two-dimensional ultrasound images of the prostate 12. As shown, the probe 10 may be operative to automatically scan an area of interest. In such an arrangement, a user may rotate the acquisition end 14 of the ultrasound probe 10 over an area of interest. Accordingly, the probe 10 may acquire plurality of individual images while being rotated over the area of interest. See FIGS. 2A-B. Each of these individual images may be represented as a two-dimensional image. See FIG. 2A. Initially, such images may be in a polar coordinate system. In such an instance, it may be beneficial for processing to translate these images into a rectangular coordinate system. In any case, the two-dimensional images may be combined to generate a 3-D image. See FIG. 2B.

As shown in FIG. 1A, the ultrasound probe 10 is a side-fire probe that generates ultrasound waves out of the side surface. However, it will be appreciated that end-fire scan probe may be utilized as well. In any arrangement, the probe 10 may also include a biopsy gun (not shown) that may be attached to the probe. Such a biopsy gun may include a spring driven needle that is operative to obtain a core from desired area within the prostate. In this regard, it may be desirable to generate an image of the prostate 12 while the probe 10 remains positioned relative to the prostate. If there is little or no movement between acquisition of the images and generation of the 3D image, the biopsy gun may be positioned to obtain a biopsy (or perform other procedures) of an area of interest within the prostate 12. However, manual manipulation of the probe 10 often results in relative movement between the probe and the prostate 12 between subsequent images and/or as a biopsy device is guided toward an area of interest.

Figure 1B:
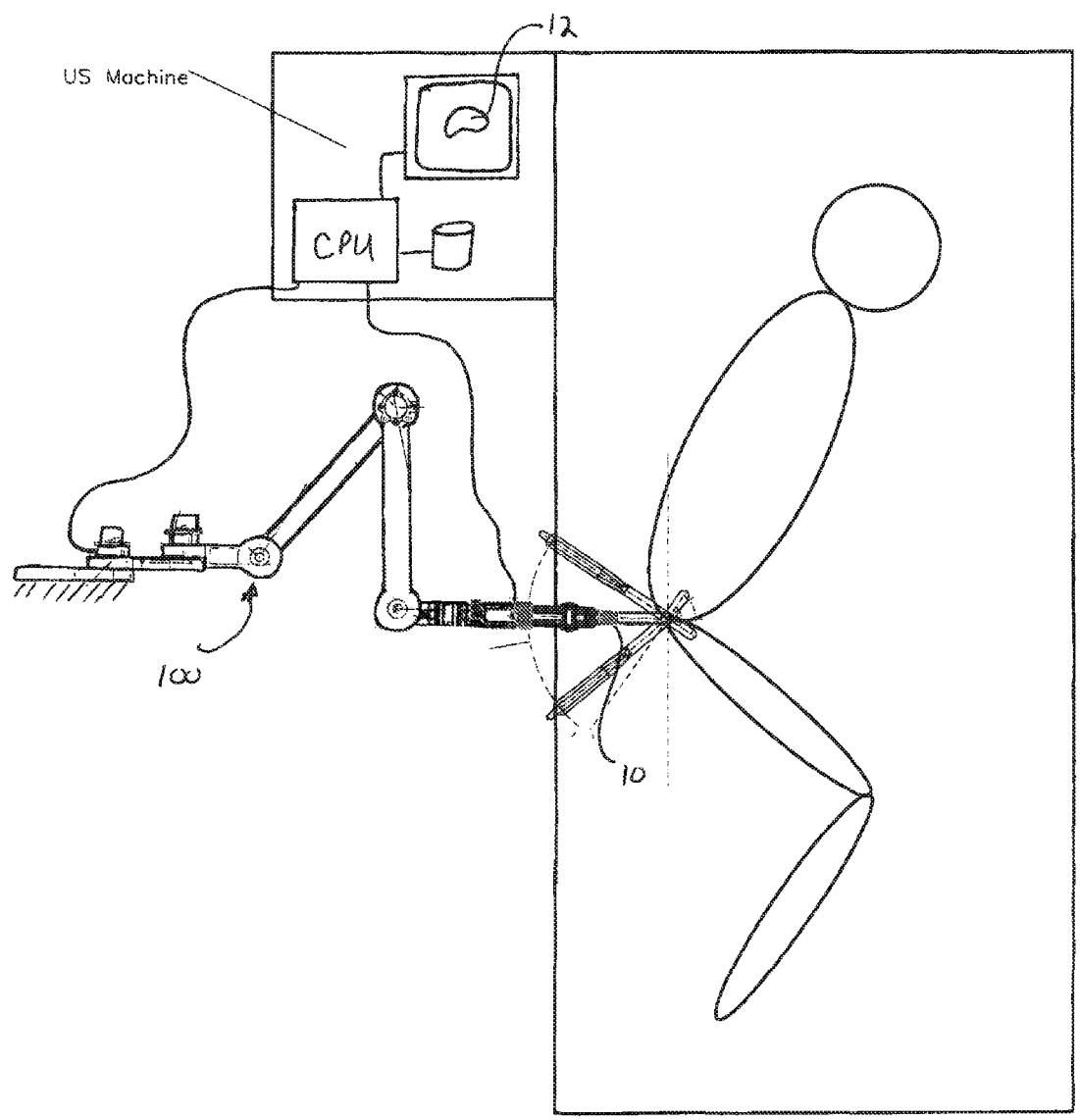
FIG. 1B illustrates use of a positioning/tracking device to position an ultrasound imaging device to perform prostate imaging.

Accordingly, for imaging is desirable that relative movement (e.g., wobble) between the probe 10 and the prostrate 12 be minimized (i.e., other than rotational movement of the probe about a fixed axis for image acquisition). Further, it is often desirable that the probe remains fixed relative to the prostrate 12 during biopsy or other treatment procedures such that desired tissue locations may be accurately targeted. To achieve such fixed positioning of the probe, it is often desirable to interface the probe 10 with a positioning or tracker assembly 100 (See FIG. 1B) that maintains the probe 10 in a fixed relative position to the prostate as well as providing location information (e.g., frame of reference information) for use with an acquired image. In this regard, location outputs of the tracker assembly may be supplied to a computer and/or imaging device. Likewise, the output of the probe may be provided to the computer and/or imaging device. Accordingly, the imaging device may utilize this information to produce an output (e.g., display) of imaged object (e.g., prostate).

FIG. 4 illustrates a tracker assembly in accordance with various aspects of the invention. As shown, the tracker assembly 100 comprises four linkages that allow for positioning a free end of the linkage including a holder and a probe 10 to a desired position relative to a patient. In this regard, the linkage assembly interfaces with a holder assembly 40 that securely holds a probe 10 in a desired orientation relative to the tracker assembly. As will be more fully discussed herein. The tracker assembly allows the interfaced holder assembly 40 to rotate about an insertion axis of the probe when the probe is inserted into the rectum of a patient. Furthermore, the tracker assembly may generate position information utilizing encoders associated with each linkage of the assembly 100 such that the position of the probe 10 and, hence, acquired images may be registered to a known field of reference.

Holder Assembly

In order to utilize a probe 10 with the tracking assembly as illustrated in FIG. 4, it is necessary to secure the probe 10 to the assembly. That is, an interface between the probe and tracking assembly is required. Complicating the interfacing of an ultrasound probe with a positioning/tracking assembly is the fact that probes made by different probe manufacturers have different dimensions. For instance, FIG. 3 illustrates an exemplary TRUS probe 10. As shown, the probe includes an insertion end 14 having a first length $L_1$ (i.e., insertion length) and a first diameter $D_1$ (i.e., insertion diameter). The insertion end along the long axis of $L_1$ defines a desired rotation axis (i.e., insertion axis). The probe 10 also includes a handle 16 having a second length $L_2$ (i.e., a holding length) and a second diameter $D_2$. Further, the probe may have a transition 18 between the insertion end 14 and handle 16. In the present embodiment, the overall length of the probe 10 is defined by the combined lengths of these components, 14, 16 and 18.

However, the dimensions (e.g., lengths and/or diameters) of any or all of these components 14, 16 and 18 may vary between probes of different manufactures. Further, these components may be tapered and/or set at an angle to one another. Therefore, to interface different probes to a common positioning device typically requires individual probe interfaces. Accordingly, provided herein is a simplified probe holding assembly that may be securely connected to a tracker assembly, where the holding device utilizes a standardized interfaces to securely hold individual probe interfaces for differently configured probes.

Figure 5A:
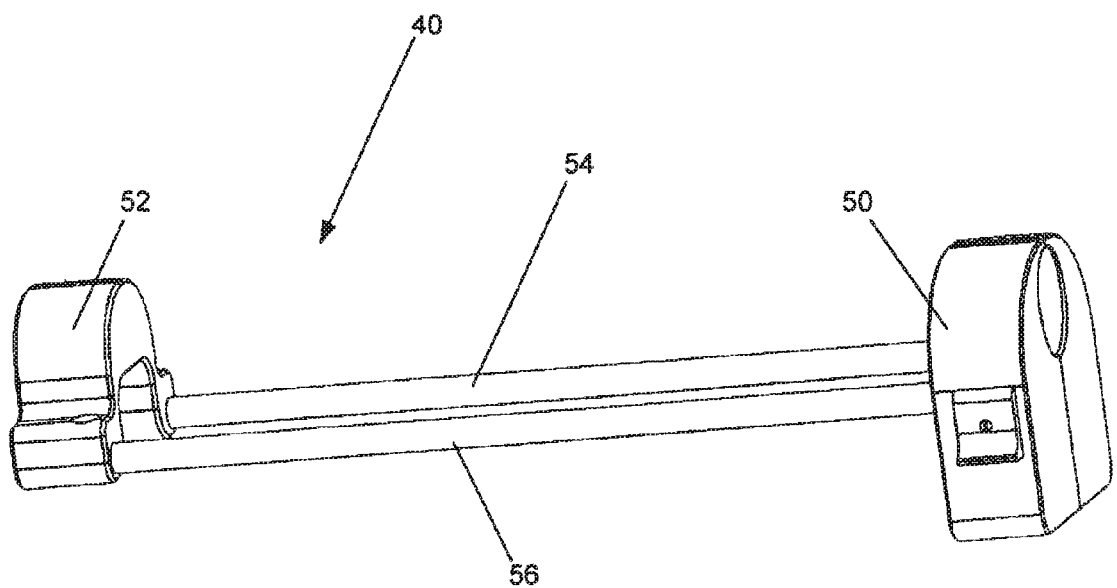
FIGS. 5A-5C illustrate an ultrasound holder.
Figure 5B:
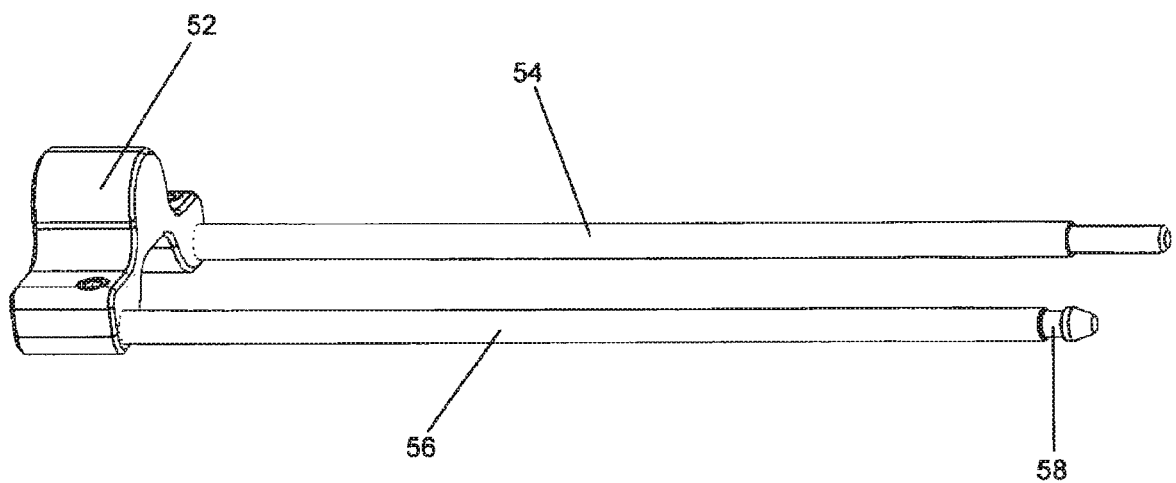
Figure 5C:
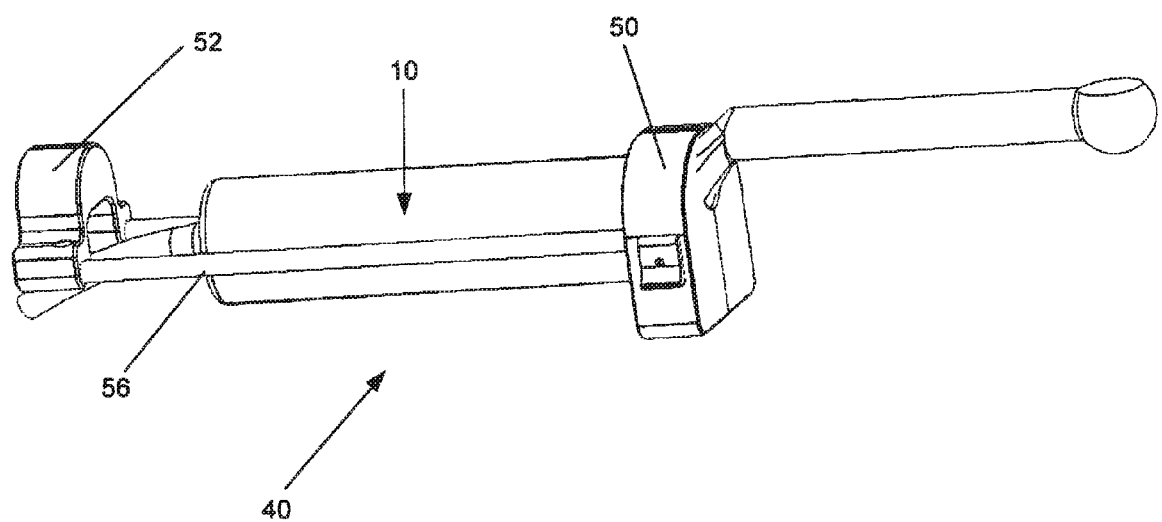

FIGS. 5A-5C illustrate a holder assembly 40 or "cradle" that may be utilized to hold differently configured ultrasound probes. As shown, the holder assembly 40 includes a collar 50 that is adapted to be positioned about a portion of an ultrasound probe 10. In this regard, the collar 50 defines an aperture having inside surfaces that are tailored to match the outside surface of an individual probe. In this regard, different probes of different OEM manufactures will utilize different collars. However, the collars have a standardized interface that allows each collar and a supported probe to be engaged with the remainder of the holder assembly. In this regard, a selected collar 50 is releaseably interconnected to a shaft connector 52 by first and second rods 54, 56. These rods 54, 56 extend along the handle portion of the probe 10, when the probe is inserted within the collar 50. It will be appreciated that the rods 54, 56 may be replaced by any connecting member (e.g., bars, plates, etc.). However, it is desirable that any connecting member utilized allows for a user to grasp the handle and/or rods 54, 56 such that a user may position the probe 10 relative to a patient.

The shaft connector 52 includes a rotational axis (not shown) on a rearward end thereof that is adapted to connect to a mating shaft 110 of the tracker device 100. Accordingly, once the shaft connector 52 of the holder assembly 40 is interconnected to the shaft 110, the holder assembly and a probe supported thereby may be rotated around the rotational axis 112 of the shaft 110. Importantly, the rotational axis 112 of the shaft 110 is aligned with the insertion axis of the probe 10. That is, individual collars for individual probes are designed such that they maintain the insertion axis of the probe aligned with the rotational axis of the tracker assembly 100, when the holder assembly 40 is connected to the tracker assembly 100.

The proximal end of the rod members 54, 56 are received within mating apertures within the shaft connector 52. As will be appreciated, such apertures may be threaded, utilize a snap-fit configuration, a press fit configuration or utilize setscrews to secure the rods therein. What is important is that the rods 54, 56 are secured within the apertures within the shaft connector 52 such that a collar 50 and probe 10 may be securely interconnected to the tracker assembly 100.

The distal ends of the connecting rods 54, 56 are releaseably received within mating apertures within the collar 50. See FIG. 6A. As different collars may be utilized with different probes, it is desirable that the collar 50 be easily removable from the connecting rods 54, 56 such that different collars and different probes may be mated with the remainder of the holder assembly 40 and hence the tracker assembly. In one arrangement, the distal ends of the connecting rods 54, 56 utilize a snap-fit arrangement. See FIG. 5B. In such an arrangement, one or both of the distal ends of the rods 54, 56 may include one or more detents 58 that may be engaged by, for example, spring-loaded retention elements within mating apertures of a collar. However, it will be appreciated that any releasable connection between the collar 50 and rods 54, 56 may be utilized and is considered within the scope of the invention. Furthermore, it will be appreciated that the rods 54, 56 may be permanently connected to the apertures within the collar and may be releaseably interconnected to the shaft connector 52.

Figure 6A:
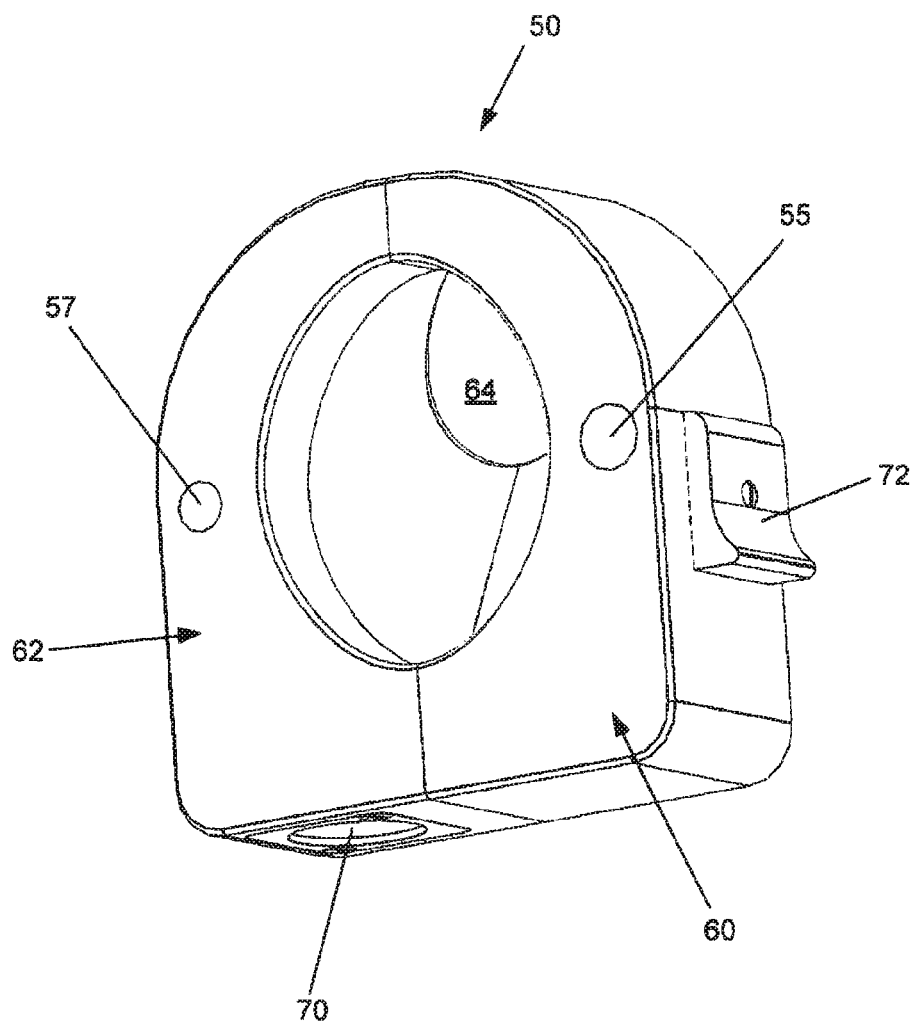
FIGS. 6A and 6B illustrate a collar portion of the ultrasound holder.

FIG. 6A illustrates a perspective view of the collar 50. As shown, the collar 50 includes first and second mating members 60, 62 that collectively define a probe receiving aperture 64. In this regard, the inside recessed surfaces of the first and second members 60, 62 that define the receiving aperture 64 are shaped to conform to a particular ultrasound probe. In order to mount the probe within the aperture 64, the first and second members 60, 62 may be separated. In this regard, the members may be made for releasable interconnection.

Figure 6B:
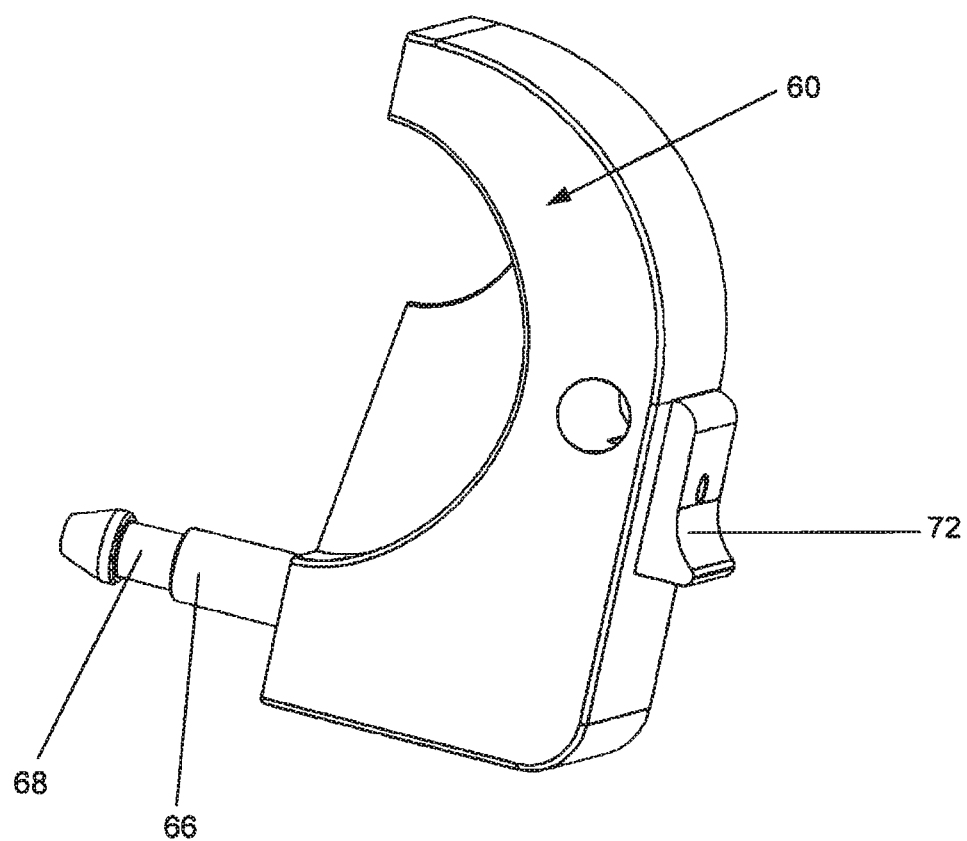

FIG. 6B shows the collar 50 having one of the members 62 removed for purposes of illustration. As shown, the remaining member 60 includes a pin 66 having one end fixably interconnected within the bottom portion of the first member 60. This pin 66 is adapted for receipt within a matching aperture within the second member 62 (not shown). As shown, the pin 66 includes a detent area 68. This detent area 68 may be engaged by a spring-loaded retention element within the second member 62. As shown in FIG. 6A, the second member 62 includes a pushbutton 70 for releasing a retention element that engages the detent area 60 of the pin member 66. Likewise, the first member 60 includes a pushbutton 72 for releasing the distal end of a mating connecting rod. In this regard, it will be appreciated that one of the connecting rods (e.g., 54) includes a distal end having a recessed detent area 58 that may be engaged by a spring retention element in the first member 62 and released by the second pushbutton 72. In the illustrated arrangement, the other connecting rod 56 has a cylindrical distal end that is received in a slip fit arrangement in an aperture in the second collar member 62.

Utilization of the connecting pin 66 and retention element mechanism 70 allows for separating the first and second collar members 60, 62. Accordingly, when separated, a probe 10 may be disposed between the members 60, 62, and the members 60, 62 may be connected while the probe is disposed therebetween. See, for example, FIG. 5C. Accordingly, as the inside surfaces of the first and second members 60, 62 are conformal with the outside surface of the probe 10, a secure interconnection may be formed between the probe and the collar 50. Further, the inside surfaces of the members 60, 62 may be textured and/or include compressible surfaces (e.g., rubberized surfaces, etc.) to firmly engage the outside surface of the probe. Such compressible surfaces may include compressible materials and/or spring-loaded plates. Exemplary compressible surfaces for use in applying a holding force to an ultrasound probe are disclosed in U.S. patent application Ser. No. 11/691,150, entitled "Universal Ultrasound Holder and Rotation Device," having a filing date of Mar. 26, 2007, the entire contents of which are incorporated by reference herein. Once the collar members 60, 62 are engaged around a probe, the probe and collar may be engaged with the connecting rods 54, 56 such that the probe is securely engaged with the holder assembly 40 and/or with the tracker assembly 100.

It will be appreciated that an imaging facility (e.g., hospital, doctor's office, etc.) may have a plurality of differently configured collars 50 that are adapted for use with a plurality of different probes that may be produced by different manufacturers. In this regard, an associated method may include selecting a collar for use with a particular probe, engaging the collar with the probe and engaging the probe with the tracker assembly prior to performing an imaging session.

Figure 7:
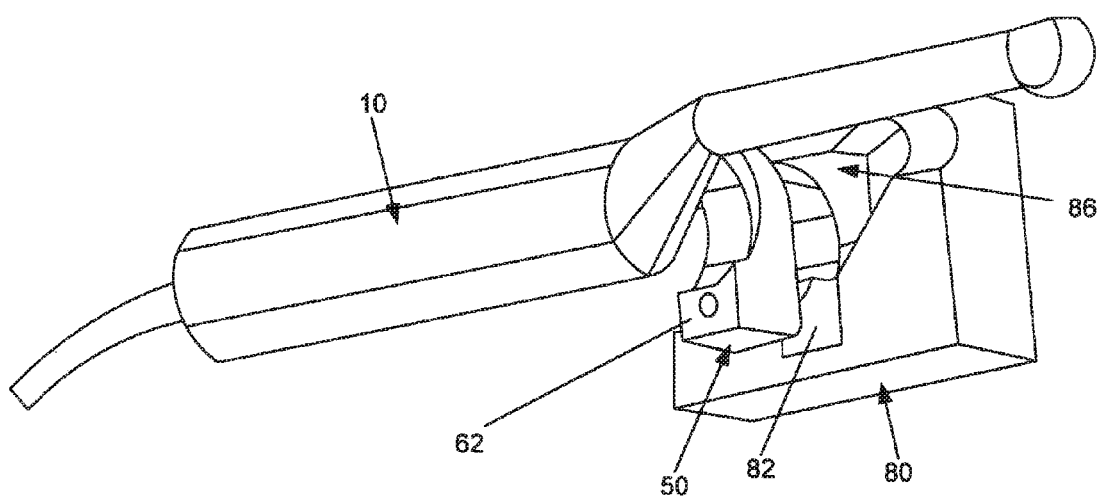
FIG. 7 illustrates a positioner for use in positioning the collar of FIGS. 6A and 6B relative to an ultrasound probe.

FIG. 7 illustrates a fixture 80 that is utilized to align a collar 50 with a probe 10. It will be appreciated that, in order for a collar 50 to accurately hold a probe 10 such that the insertion axis of the probe is aligned with the rotational axis 112 of the tracker assembly 100, precise alignment of the collar with the probe is required. The fixture 80 is utilized to accurately align the collar and the probe. As shown, the fixture 80 has a recessed interior surface that is shaped in accordance with the outside configuration of a particular probe. In this regard, it will be appreciated that each fixture 80 is designed for an individual probe. In addition, the fixture 80 includes a slot 82 that is sized to receive the outside edge of one member of a collar 50. In this regard, the collar 50 may be placed within the slot 80, and the probe 10 may be aligned within the recess 86 within the fixture 80. In this regard, once the probe is placed within the recess 86 of the fixture 80, it is correctly aligned with one member of the collar. Accordingly, the other member of the collar may be connected to the member disposed within the fixture. This allows for accurately aligning the collar 50 with the correct location on the probe.

Tracker Assembly

The tracker assembly tracks the coordinates of an instrument (i.e., probe) in 3D space. Furthermore, the present tracker assembly 100 also supports the probe and provides orientation of the probe for an interconnected imaging system. The tracker assembly also measures the rotation of the probe around the rotational axis 112. As shown in FIGS. 4 and 8A-8F, the tracker is composed of various linkages $N_1$-$N_5$ defined by rigid arms that are hingedly connected by rotating joints 122-130 that have well-specified degrees of motion. Encoders between each joint 122-130 of the linkages $N_1$-$N_5$ are operative to provide an output indicative of the movement between those linkages. The holder assembly 40 is mounted to the rotational shaft 110 of the last linkage $N_5$ tracker assembly 100.

The holder assembly secures the probe such that the geometry of the probe relative to the tracker assembly is fixed. It will be appreciated that such a tracker assembly can be used in any application where tracking of an instrument improves the accuracy of a procedure such as, for example, image-guided surgery, image-guided biopsy, image-guided therapy, etc. Though presented herein for use in prostate biopsy, it will be appreciated that the tracker assembly may be utilized in other applications.

The tracker assembly is a device that has five linkages $N_1$-$N_5$ and six degrees of freedom. Positional measurement of the tracker assembly 100 is done by encoders that measure angles of rotation between each linkage $N_1$-$N_5$. That is, the encoders measure the rotation of the linkages about the various axes $I_1$-$I_6$. Geometric principles may then be used to compute the tracking data (i.e., positional information) from the encoder measurements.

The linkages of the tracker assembly 100 may be formed of any material that provides adequate stiffness. For instance, such materials may include, without limitation, metals, plastics and/or composite materials. What is important is that the selected materials be rigid enough to maintain accurate positioning of the supported probe 10. In any case, the system allows for five degrees of motion ($I_1$-$I_5$) for positioning a probe and a sixth degree of motion ($I_6$) around the rotational shaft 110 for rotating a probe. Each of the five linkages $N_1$-$N_5$ are interconnected via a hinged element/joint, as will be more fully discussed herein. In addition, a base link $N_0$ defines a references axis 120 (e.g., reference axis/point of a global coordinate system) from which the position of the distal end of the assembly may be determined.

The base link $N_0$ may be affixed to a structure such as exam room bed or a portable equipment cart. A first end of the first link $N_1$ is interconnected to the base link $N_0$ about a first joint 122. Likewise, the remainder of the linkages are interconnected utilizing additional joints 124-130. As shown, the first and second joints 122, 124 are perpendicular to the joints 126-130. This allows positioning the supported probe in three dimensions.

Interconnected to the end of the fourth linkage $N_4$ is the holder assembly mounting linkage $N_5$. The holder assembly mounting linkage $N_5$ includes the rotational shaft 110 to which the holder assembly 40 is mounted. Accordingly, once the holder assembly 40 is interconnected to the shaft 110, it may be rotated about the rotational axis 112. This rotational axis 112 provides the sixth degree of freedom ($I_6$) for the tracker assembly. In summary, the linkage assembly $N_1$-$N_5$ supports the probe 10 through rotating joint connections 120-130 while the holder assembly supports the probe such that the longitudal axis of the probe is collinear with the rotational axis 112. Therefore, the angular position of the axis of the probe relative to the base member and the global coordinate system may be determined. That is, the position of the probe is determined by the angles between each pair of links $N_1$-$N_5$ in combination with the lengths of the links.

In order to measure the angular displacement of each of the linkages $N_1$-$N_5$, six encoders are used to measure the relative angles between each linkage $N_1$-$N_5$. The encoders for the tracker assembly are incorporated into the various joints 122-130. In one arrangement, the encoders may be formed from off the shelf rotary encoders having a high accuracy. For instance, such accuracy may be 13 bits to provide 8,192 positions per revolution. One supplier of such rotary encoders is Renishaw Inc. of Chicago, Ill. However, it will be appreciated that other encoders including encoders produced by other manufacturers may be utilized as well. This accuracy in turn may determine the tracking accuracy of the tracker assembly 100.

Generally, the encoders include a magnetic actuator and a separate encoder body. In this regard, the magnetic actuator (e.g., magnet) may be mounted to a shaft of the rotational axis that is disposed within an encoder body. In this regard, each joint may include a joint axel that includes a shaft and magnetic actuator. The joint axel may be received in bores formed on the ends of the linkages. Such bores may include appropriate bushing, bearing etc. The encoder body may be mounted within the end of the linkages (e.g. proximate to and/or around the bore). In any case, the rotation of this magnet is sensed by an encoder chip within the body and processed to give the required output. As will be appreciated, each encoder will be interconnected to a computational device (e.g., imaging device, CPU, PC, etc.) utilizing appropriate wiring connections. However, such wiring connections are not shown in the present embodiment to simplify the illustration of the tracker assembly 100. In one arrangement, a commercial encoder interface (USB1, US digital) is used to read the encoder values. For example, a USB1 device may send data to a computer through a USB port and a DLL interface. The transformation between the image frame of reference and the tool frame of reference, which is typically the ultrasound transducer, may be performed by the client application. In any case, this allows for providing base frame of reference for use with the acquired images.

Figure 9:
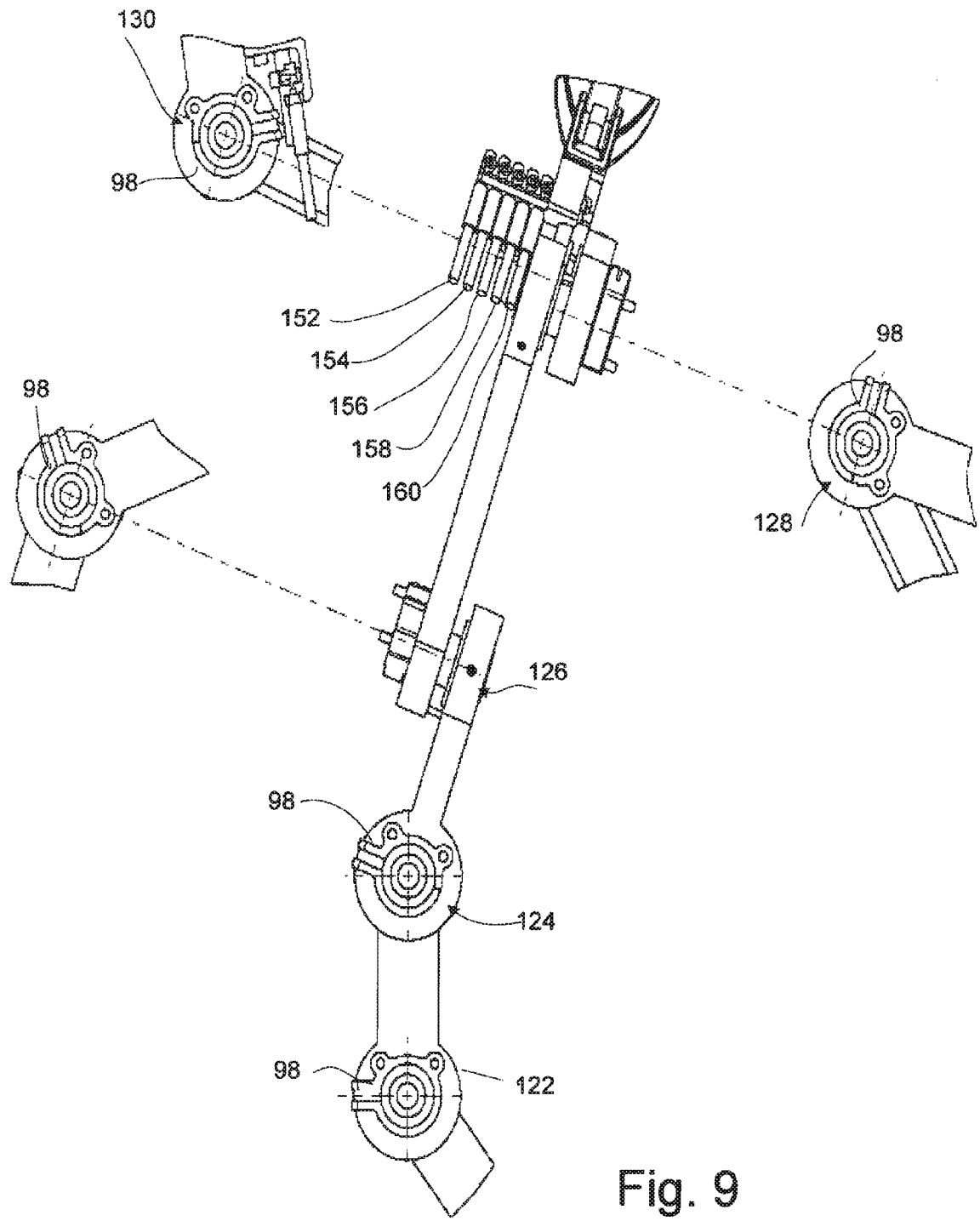
FIG. 9 illustrates a braking assembly utilized with the joints of the tracker assembly.

In addition to providing an output of the location of the distal end of the assembly, each of the joints 122-130 further includes mechanical braking assembly. See FIG. 9. In this regard, once the tracker assembly and probe are positioned to a desired location, these braking assemblies may be locked in order to maintain the tracker assembly at a fixed position. At such time, the probe 10 may be rotated around the rotational axis 112 to provide images having a fixed reference frame. In one arrangement, the braking mechanism simultaneously prevents the movement of the five joints 120-130 and hence linkages $N_1$-$N_4$.

In the present embodiment, the braking assembly is actuated utilizing a brake lever 150. See FIG. 4. The brake lever 150 is interconnected to the braking mechanism at each joint 120-130 via a braking cable. These braking cables 152-160 extend from the brake lever 150 to a respective one of the braking mechanisms associated with each of the hinges 120-130. See FIG. 9. The cables 152-160 are not shown to facilitate illustration of the tracker assembly 100. In any case, engaging the brake lever 150 applies tension in each of the five braking cables. This tension acts on the rotary brake members 98, reduces their inner diameter. The reduction in diameter introduces a friction force on the bearing components (i.e., joint axel), preventing rotation of the joint.

Accordingly, once the lever 150 is depressed, the tracker assembly is substantially fixed relative to the global coordinate system.

In addition to braking, the tracking assembly is also counter-balanced through use of spring loading at the hinges or counter-balancing weights. The counter balancing allows the user to freely maneuver the free end of the assembly without feeling weight of the assembly. Also, counterbalancing ensures that the assembly stays in position without need for a lock. Further the counterbalancing ensures that once released by the operator, the device not fall off to the ground (e.g., collapse). In this regard, the counterbalancing allows the tracker assembly to be self-supporting.

Figure 10:
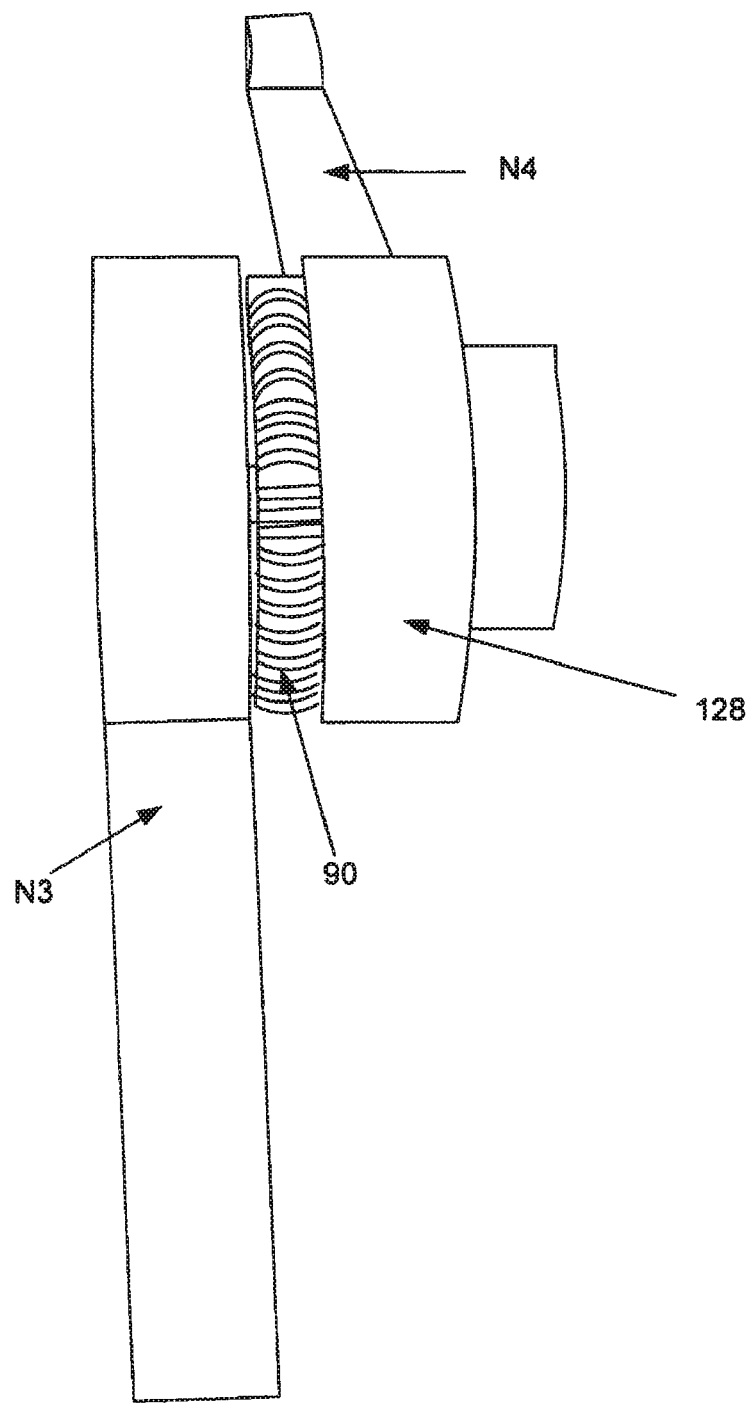
FIG. 10 illustrates a spring loading assembly utilized with the joints of the tracker assembly.
Figure 11:
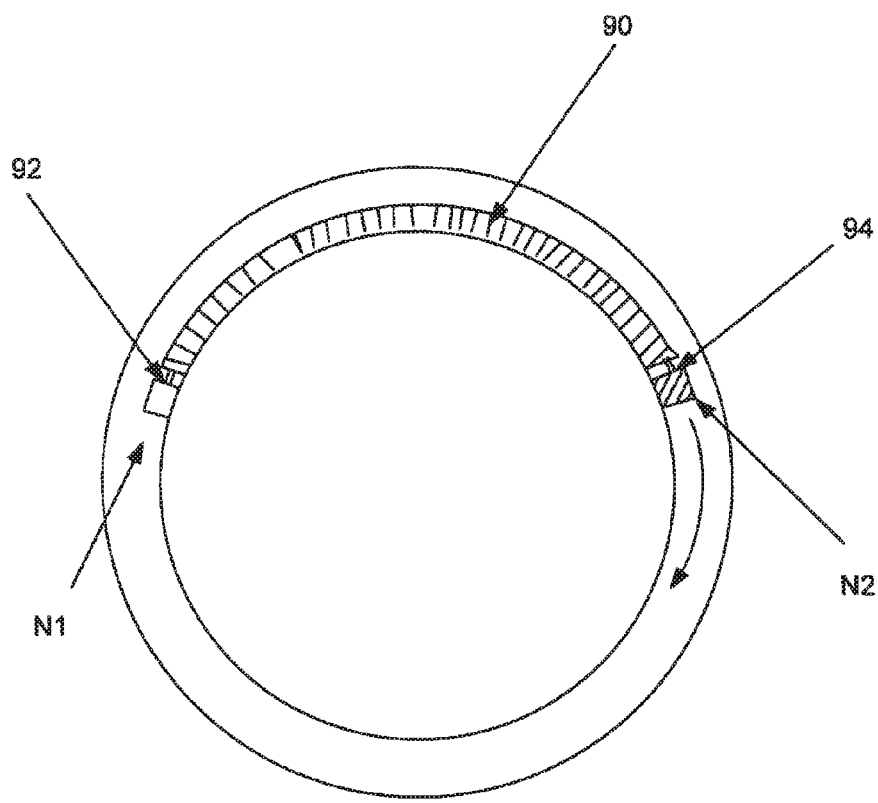
FIG. 11 illustrates a side view of the spring loading assembly.

FIGS. 10 and 11 illustrate one embodiment of a counterbalancing arrangement where a spring 90 is incorporated into a joint 128 between two link members $N_3$ and $N_4$. As shown, the spring 90 extends around a portion of the joint 128. That is, the spring 90 wraps around the axel (not shown) of the joint. A first end 92 of the spring 90 is interconnected to a first link member $N_3$ via a first pin member 93 and a second end 94 of the spring 90 is interconnected to the second link member $N_4$ (not shown in FIG. 11) via a second pin member 95. Accordingly, the spring 90 may be stretched when the link members rotate relative to one another. The resulting resistance provided by the spring may provide a force that maintains a new angular position between the link members. As will be appreciated, each joint may incorporate a similar counterbalancing arrangement.

Figure 8A:
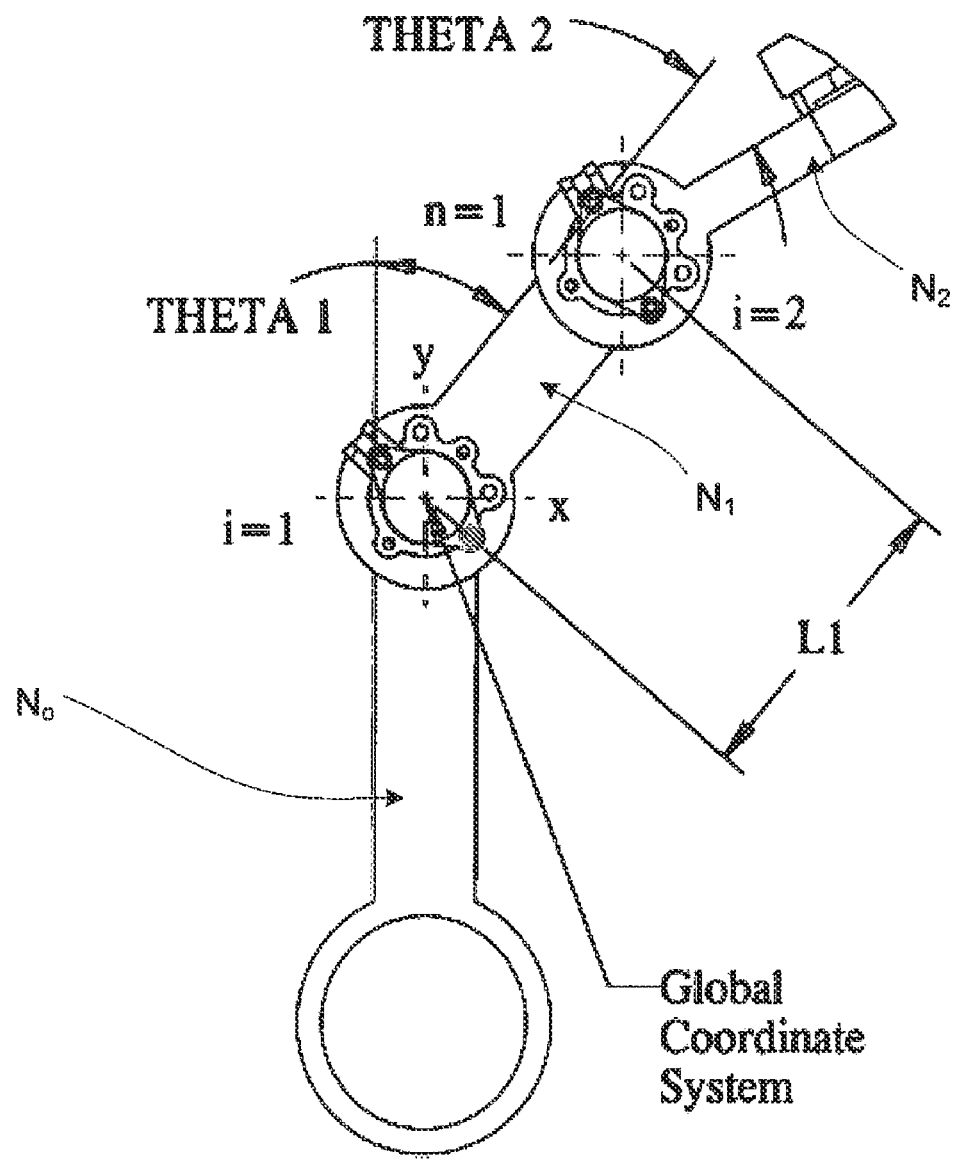
Figure 8B:
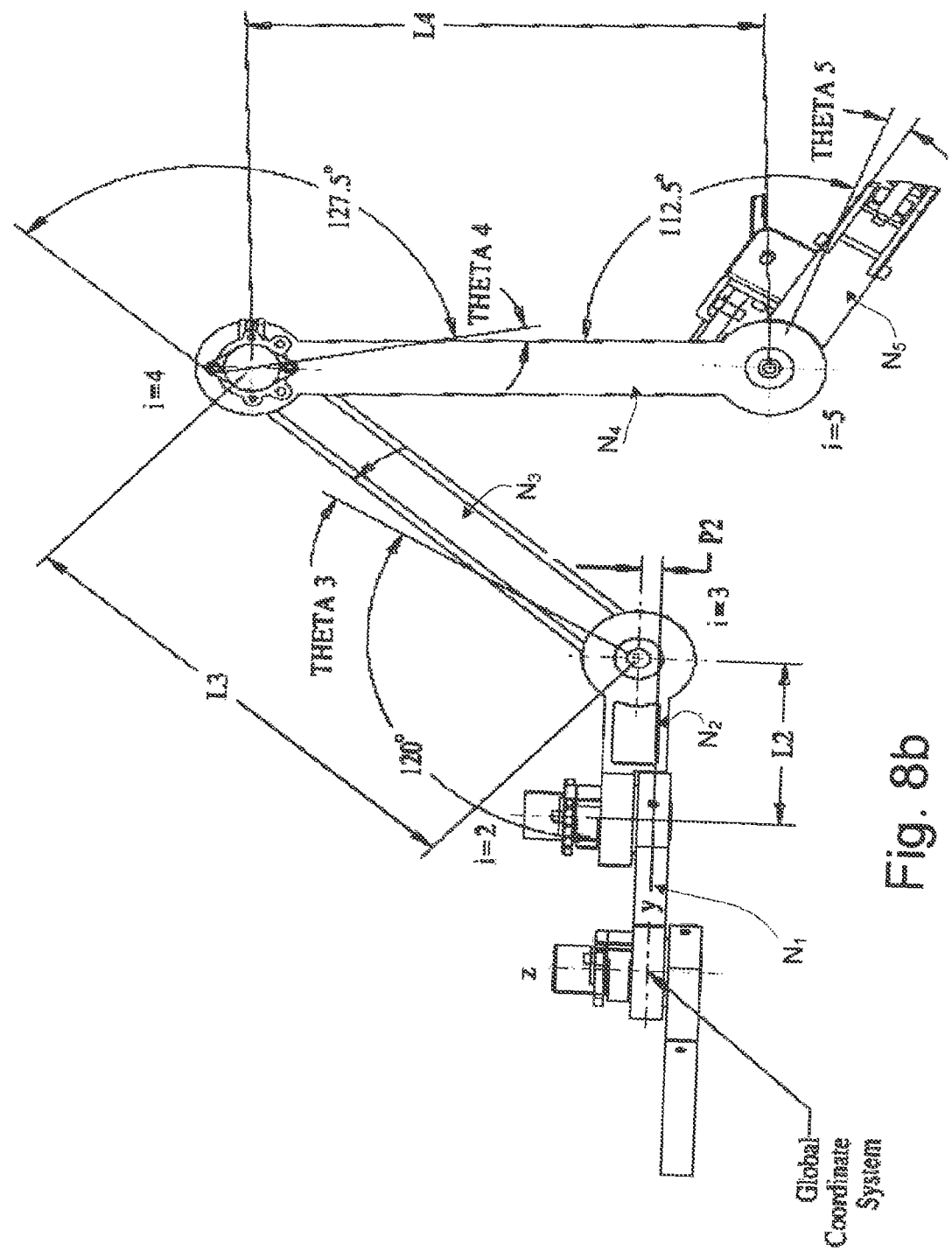

FIGS. 8A-8C illustrate the dimensions of the tracker assembly 100 as they are utilized to mathematically determine the location of the distal end of a probe interconnected to the holder assembly 40. The location and heading of the probe reference point (e.g., probe tip) with respect to the global coordinate system are functions of the angles of the linkage members and the lengths of and offsets between the linkage members. Angles $\theta_1$, $\theta_2$, $\theta_3$, $\theta_4$, and $\theta_5$ represent the angles of the linkage members relative to each proceeding member. Each linkage member angle is measured with respect to an encoder zero-position that has been calibrated to correspond to the center of the range of motion for each joint. A graphical representation of the linkage member angles is depicted in FIGS. 8a through 8c. These Figures also depict the relevant lengths and offsets that are used to calculate the probe reference point location and heading.

The following equations represent the location of the TRUS reference point relative to the global coordinate system:

$$\begin{Bmatrix} x \\ y \\ z \end{Bmatrix} = \begin{Bmatrix} L_1\sin(\theta_1) + \left[\begin{array}{c} L_2 + L_3\sin(30° + \theta_3) + \\ L_4\sin\beta + L_5\sin\gamma \end{array}\right]\sin(\theta_1 + \theta_2) - P_5\sin\delta \\ L_1\cos(\theta_1) + \left[\begin{array}{c} L_2 + L_3\sin(30° + \theta_3) + \\ L_4\sin\beta + L_5\sin\gamma \end{array}\right]\cos(\theta_1 + \theta_2) + P_5\cos\delta \\ P_2 + L_3\cos(30° + \theta_3) - L_4\cos\beta - L_5\cos\gamma \end{Bmatrix} \quad \text{Eq. (1)}$$

where $$\beta = 22.5° - \theta_3 - \theta_4$$

$$\gamma = 90° - \theta_3 - \theta_4 - \theta_5$$

$$\delta = 90° - \theta_1 - \theta_2$$

The following equations represent the unit vector parallel to the TRUS assembly axis:

$$\vec{u} = \begin{Bmatrix} \sin\gamma\sin(\theta_2 + \theta_2) \\ \sin\gamma\cos(\theta_1 + \theta_2) \\ -\cos\gamma \end{Bmatrix} \quad \text{Eq. (2)}$$

As shown, the length of each linkage $L_1$-$L_4$ is fixed. Furthermore, the angular displacement of each linkage relative to the other linkages may be determined by the encoder as $\theta_1$-$\theta_4$. Finally, it will be noted that the final length $L_5$ between the tip of the ultrasound probe 10 and joint 130 may vary between probes. That is, probes of different lengths may have a different $L_5$ length. Accordingly, the user may input information associated with this length as provided for each individual probe. In any case, the mathematical calculation of the distal tip of the probe allows for quickly updating location/positional information for the probe. Furthermore, once the tracker assembly 100 is fixed relative to a desired location, angular displacement around the rotational axis 110 may be recorded in conjunction with obtaining images as the probe is rotated.

That is, during image acquisition, it is typical to insert the insertion end of the ultrasound probe relative to a tissue area of interest (e.g., the prostrate). Once so positioned, the probe may be rotated while a plurality of 2-1) images are obtained for use in generating a 3-D image. The images may be acquired at equal angular offsets in order to provide an improved 3-D image. To allow equal angular offsets, the probe rotation may be motorized or utilize a ratchet and pawl arrangement such as set forth in U.S. patent application Ser. No. 11/691,150, as incorporated above.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in similar or other embodiments and with various modifications required by the particular application(s) or use(s) of the present invention. It is intended that the appended claims be construed to include alternative embodiments to the extent permitted by the prior art.

What is claimed:

1. A device for positioning and tracking in three dimensions the position of an ultrasound imaging probe, comprising:
   a base element;
   a linkage of at least three rigid arms, wherein said rigid arms are hingedly connected and a first end of the linkage is hingedly connected to said base element and a second end of said linkage is a free end that is operative to move in three dimensions;
   encoders disposed between each hinged connection of said linkages and said base element, wherein said encoders generate an output indicative of an angular position of hingedly connected arms;
   a rotational shaft interconnected to the free end of said linkage; and
   an encoder operative to generate an output indicative of rotation of said rotational shaft about a rotational axis:

an ultrasound probe holder attached to said rotational shaft for releasable holding an ultrasound probe;

an ultrasound probe releasably interconnected to said ultrasound probe holder, said ultrasound probe having an elongated acquisition end designed for insertion into a patient orifice and a probe handle, wherein the acquisition end is offset from the handle end and wherein the ultrasound probe holder engages the probe handle to align a long axis of the acquisition end with the rotational axis of the rotational shaft;

wherein said outputs from all said encoders provide information for calculating a location of said acquisition end of said probe relative to said base element.

2. The device of claim 1, wherein said linkages are counterbalanced, wherein each said hinged connection includes a spring, wherein said spring is operatively connected to each linkage associated with said hinged connection.

3. The device of claim 1, wherein each hinged connection adds a degree of freedom and extension to the free end of said linkage.

4. The device of claim 1, wherein said holder comprises:

an interface element for connecting with said rotational shaft; and a collar for securely fastening around at least a portion of an ultrasound probe, wherein said collar is releasably connectable with said interface element.

5. The device of claim 1, wherein said linkage comprises five linkages.

6. The device of claim 5, wherein said linkage include five hinged connections and an end linkage defining said free end of said linkage includes a said rotational shaft, wherein said five hinged connections and said rotational shaft permit the free end of said linkage to move with six degrees of freedom.

7. The device of claim 1, wherein each hinged connection comprises a joint, wherein each joint limits connected members to movement about a single axis.

8. The device of claim 6, wherein at least first and second joints define a first set of parallel axes and at least third and fourth joints define a second set of parallel axes, wherein said first and second sets of axes are transverse.

9. The device of claim 8, wherein each said joint further comprises:

a brake, wherein said brake is selectively operable to prevent movement of said joint.

10. The device of claim 9, further comprising:

a brake actuator for simultaneously actuating brakes of all joints.

11. The device of claim 1, wherein said encoders comprise a magnetic encoder.

12. The device of claim 11, wherein said magnetic encoder has at least 12 bit resolution.

* * * * *